(12) United States Patent
Bringhen et al.

(10) Patent No.: US 6,416,746 B1
(45) Date of Patent: Jul. 9, 2002

(54) INDANYLIDENE COMPOUNDS

(75) Inventors: Alain Bringhen, Choulex; Ulrich Huber, Erlenbach, both of (CH)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/438,199

(22) Filed: Nov. 11, 1999

(30) Foreign Application Priority Data

Nov. 11, 1998 (EP) .............................................. 98121456

(51) Int. Cl.[7] ................................................ A61K 7/42
(52) U.S. Cl. ......................................... 424/59; 424/401
(58) Field of Search .................... 424/59, 401; 252/589

(56) References Cited

U.S. PATENT DOCUMENTS 5,965,066 A * 10/1999 Koch et al. .................. 252/489

FOREIGN PATENT DOCUMENTS

| EP | 0 823 418 A2 | 2/1998 |
| WO | WO 91/16892 | 11/1991 |
| WO | WO 99/09112 | 2/1999 |

OTHER PUBLICATIONS

Chan and Roth,"2,4–Diamino–5–benzylpyrimidines as Antibacterial Agents. 14. 2,3–Dihydro–1–(2, 4–diamino–5–pyrimidyl)–1H–indenes as Conformationally Restricted Analogues of Trimethoprim," *J. Med. Chem.*, vol. 34, pp. 550–555 (1991).

Bhattacharyya, et al., "Selective Reduction of Dienones Synthesis of Intermediates For Sesqui–and Diterpenes," *Synthetic Communications*, vol. 19, No. 3 & 4, pp. 673–678 (1989).

Basu, et al., "Studies on Intramolecular Cyclisations. Synthesis of Ring Systems Related to Sesquiterpenoids," *Synthetic Communications*, vol. 11 (10), pp. 803–809 (1981).

Crooks and Sommerville, "The Synthesis and Analgesic Activities of Some Spiro[indan–1,3+e,acu +ee –pyrrolidine] Derivatives Designed as Rigid Analogs of Profadol," *Journal of Pharmaceutical Sciences*, vol. 71, No. 3, pp. 291–294 (1982).

Das, et al., "Aryl Participated Cyclisations Involving Indane Derivatives, A Total Synthesis of (±)–Isolongifolene," *Tetrahedron Letters*, vol. 33, No. 9, pp. 1229–1232 (1992).

Chemical Abstracts, vol. 104, No. 9, Abstract No. 68709 (1986).

* cited by examiner

*Primary Examiner*—Jose' G. Dees
*Assistant Examiner*—Konata M. George
(74) *Attorney, Agent, or Firm*—Bryan Cave LLP

(57) ABSTRACT

The invention relates to novel indanylidene compounds which are effective in absorbing ultra violet radiation and to light screening compositions including the indanylidene compounds of the general formula I

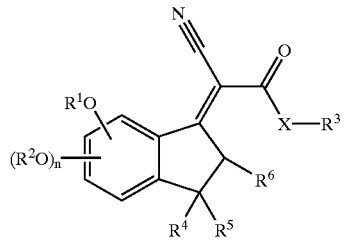

wherein
X is O or NH;
$R^1$ is a $C_1$–$C_{20}$ alkyl, $C_2$–$C_{20}$ alkyl in which at least one methylene group is replaced by oxygen, $C_3$–$C_{20}$ alkenyl, $C_3$–$C_{20}$ alkynyl or a group YS;
$R^2$ is a $C_1$–$C_{20}$ alkyl, $C_2$–$C_{20}$ alkyl in which at least one methylene group is replaced by oxygen, $C_3$–$C_{20}$ alkenyl, $C_3$–$C_{20}$ alkynyl or a group YS; or $R^1$ and $R^2$ may combine on adjacent C-atoms to form a dioxomethylene ring;
$R^3$ is a $C_1$–$C_{20}$ alkyl, $C_2$–$C_{20}$ alkyl in which at least one methylene group is replaced by oxygen, $C_3$–$C_{20}$ alkenyl, $C_3$–$C_{20}$ alkynyl or a group YS;
$R^4$, $R^5$, $R^6$ are each independently H or $C_1$–$C_{20}$ alkyl;
n is 0, 1 or 2;
Y is a linker group;
S is a silane-, an oligosiloxane- or a polysiloxane- moiety; with the proviso that at least one of the $R^1$, $R^2$ or $R^3$ residues is YS.

Methods for protecting skin from UV damage using a light screening agent containing one of the indanylidene compounds of the present invention are also provided.

36 Claims, No Drawings

INDANYLIDENE COMPOUNDS

FIELD OF THE INVENTION

This invention relates to novel indanylidene compounds which effectively absorb ultra violet (UV) radiation and to light screening compositions containing these indanylidene compounds.

BACKGROUND OF THE INVENTION

Light screening compositions including indanylidene compounds are reportedly disclosed in EP 0823 418 A2. This publication emphasizes cyano-(2,3-dihydroxy-1H-inden-1-ylidene) acetic acid ester compounds. These compounds, however, do not have a sufficient solubility in the media typically employed in cosmetics, in particular in oil and fats. Furthermore, it is desirable that the active ingredient remain on the surface of the skin, rather than prior art compounds that penetrate into or through the skin.

SUMMARY OF THE INVENTION

It has now been found that compounds having an indanylidene residue grafted via a linker to a silane, an oligosiloxane- or a polysiloxane moiety overcome the problem of penetration and show improved solubility compared to prior art compounds.

Accordingly, the present invention provides compounds of the general formula I:

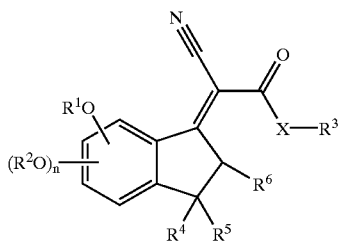

The invention also provides compositions containing these compounds, and methods of using the compounds and the compositions.

DETAILED DESCRIPTION OF THE INVENTION

The present invention provides compounds of the general formula I:

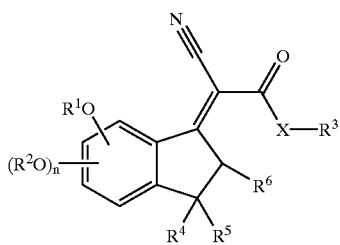

wherein
X is O or NH;
$R^1$ is $C_1$–$C_{20}$ alkyl, $C_2$–$C_{20}$ alkyl in which at least one methylene group is replaced by oxygen, $C_3$–$C_{20}$ alkenyl, $C_3$–$C_{20}$ alkynyl or a group YS;
$R^2$ is $C_1$–$C_{20}$ alkyl, $C_2$–$C_{20}$ alkyl in which at least one methylene group is replaced by oxygen, $C_3$–$C_{20}$ alkenyl, $C_3$–$C_{20}$ alkynyl or a group YS; or
$R^1$ and $R^2$ may combine on adjacent C-atoms to form a dioxomethylene ring;
$R^3$ is $C_1$–$C_{20}$ alkyl, $C_2$–$C_{20}$ alkyl in which at least one methylene group is replaced by oxygen, $C_3$–$C_{20}$ alkenyl, $C_3$–$C_{20}$ alkynyl or a group YS;
$R^4$, $R^5$, $R^6$ are each independently H or $C_1$–$C_{20}$ alkyl;
n is 0, 1 or 2;
Y is a linker group;
S is a silane-, an oligosiloxane- or a polysiloxane-moiety;
with the proviso that at least one of the $R^1$, $R^2$ or $R^3$ residues is YS.

As used herein, the phrase "$C_1$–$C_{20}$ alkyl" refers to straight chain or branched saturated hydrocarbon residues with 1–20 carbon atoms, such as for example, methyl, ethyl, propyl, isopropyl, butyl, sec. butyl, isobutyl, pentyl, neopentyl, hexyl, 2-ethyl-hexyl, octyl, and the like.

As used herein, the phrase "$C_2$–$C_{20}$ alkyl in which at least one methylene group is replaced by oxygen" refers to straight chain or branched saturated hydrocarbon residues with up to 19 carbon atoms having at least one group such as —(CH$_2$—O)—,—(CH$_2$—CH$_2$—O)—, —(CH$_2$—CH$_2$—CH$_2$—CH$_2$—O) and the like.

In the present invention, the phrase "$C_3$–$C_{20}$ alkenyl" refers to straight chain or branched unsaturated hydrocarbon residues with 3-20 carbon atoms containing a double bond, such as for example, propen-2-yl, propen-3-yl, buten-3-yl, buten-4-yl, penten-4-yl, penten-5-yl, and the like.

As used herein, the phrase "$C_3$–$C_{20}$ alkynyl" refers to straight chain or branched unsaturated hydrocarbon residues with 3–20 carbon atoms containing a triple bond such as for example, propargyl and the like.

As used herein, the phrase "linker group" refers to a $C_3$–$C_{12}$ divalent alkylene or alkenylene chain which links the silane, oligosiloxane or polysiloxane moiety to the UV absorbing chromophoric residue. In the present invention, "$C_3$–$C_{12}$ divalent alkylene chain" includes straight chain or branched saturated hydrocarbon residues, such as for example, 3-propylene, 2-propylene, 2-methyl-3-propylene, 3-butylene, 4-butylene, 4-pentylene, 5-pentylene, 6-hexylene and the like. In the present invention, "$C_3$–$C_{12}$ divalent alkenylene chain" includes unsaturated hydrocarbon residues containing one or multiple double bonds, such as for example, 2-propen-2-ylene, 2-propen-3-ylene, 3-buten-3-ylene 3-buten-4-ylene, 4-penten-4-ylene, 4-penten-5-ylene, (3-methyl)-penta-2,4-dien-4 or 5-ylene, 11-dodecen-11-ylene and the like. Such chains may be interrupted by one or several oxygen atomforming groups such as 2-ethyloxy-eth-2-ylene, 4-butyloxy-eth-2-ylene, 3,6-dioxa-8-octylene and the like. Preferred linker groups in the present invention are: 3-propylene , 4-butylene, 2-propen-2-ylene, 2-propen-3-ylene or 3-buten-4-ylene.

As used herein, the term "silane" refers to a group -Si$R^7R^8R^9$ wherein $R^7$, $R^8$ and $R^9$ are each independently $C_1$–$C_6$ alkyl, $C_1$–$C_6$ alkoxy or phenyl. The "$C_1$–$C_6$ alkyl" and "C–$C_6$ alkoxy" residues may be straight-chain or branched, such as for example, methyl, ethyl, propyl, isopropyl, n-butyl, tert. butyl, thexyl, (1,1,2 dimethylpropyl) and, respectively, methoxy, ethoxy, propoxy, isopropoxy, n-butoxy, tert. butoxy, and thexoxy for the $C_1$–$C_6$ alkoxy. Preferred are alkyl-silane groups, such as for example, trimethylsilane, triethylsilane, tripropylsilane, triisopropylsilane, dimethyl tert. butylsilane, dimethyl thexylsilane, triphenylsilane, dimethylphenylsilane, and the like.

As used herein, "oligosiloxane" refers to groups of the general formula—$SiR^{10}{}_m(OSiR^{10}{}_3)_n$ wherein $R^{10}$ is defined below and m=0, 1 or 2; n=3, 2 or 1, and m+n=3; or groups of the general formula IIa or IIb

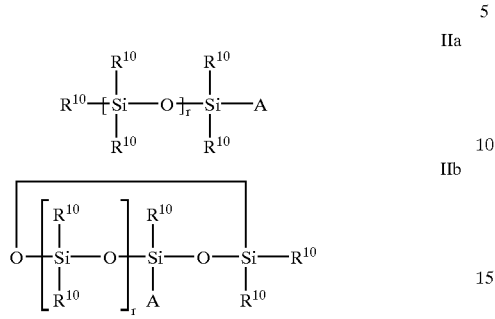

wherein

A is a bond to the linker Y;

$R^{10}$ is $C_1$–$C_6$ alkyl or phenyl;

r is 1 to 9.

In the present invention, the term "polysiloxane" refers to groups of the general formulae IIIa or IIIb:

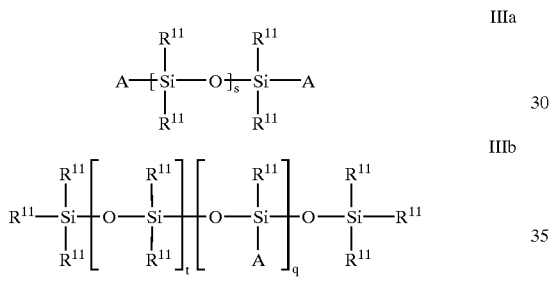

wherein

A is a bond to the linker Y;

$R^{11}$ is $C_1$–$C_6$ alkyl or phenyl;

s is from 4 to 250;

t is from 5 to 250;

q is from 1 to 30.

In the present invention, the $R^1$ and $R^2$ residues are preferably $C_1$–$C_6$ alkyl, more preferably $C_1$–$C_4$ alkyl, such as for example, methyl, or a group YS. The $R^3$ residue is preferably $C_1$–$C_6$ alkyl, more preferably $C_1$–$C_4$ alkyl, such as for example, ethyl, or a group YS.

The $R^4$ and $R^5$ residues are preferably $C_1$–$C_6$ alkyl, more preferably $C_1$–$C_4$ alkyl, such as for example, methyl.

The $R^6$ residue is preferably $C_1$–$C_6$ alkyl, more preferably $C_1$–$C_4$ alkyl, such as for example, methyl or hydrogen.

The $R^{10}$ and $R^{11}$ residues are preferably $C_1$–$C_6$ alkyl, more preferably $C_1$–$C_4$ alkyl, such as for example, methyl.

In the present invention, the value of "n" is preferably 0 or 1, "r" is preferably 1 to 3, "s" is preferably 5 to 150, "q" is preferably 2 to 10, more preferably a statistical mean value of about 4, "t" is preferably 5 to 150, more preferably a statistical mean value of about 60.

In the present invention, each $R^1$, $R^2$ or $R^3$ group may be YS. Thus, the silane-, oligosiloxane- or polysiloxane moiety may be linked via Y to the indane ring or to the carboxy or amide group. Preferably the silane-, oligosiloxane- or polysiloxane moiety is linked to the carboxy or amide group (e.g. $R^3$ is YS).

The compounds of formula I may be prepared as follows:

In a first step, compounds of formula Ia

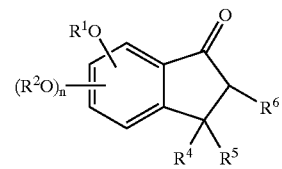

wherein $R^1$, $R^2$, $R^4$, $R^5$, $R^6$ and n are as defined above are synthesized according to known reactions (see, e.g., F. Camps, Z. Naturforsch., B: Anorg. Chem., Org. Chem. (1984), 39B (12), 1801-5), and Tetrahedron Letters 27, 2941 (1973), which are hereby incorporated by reference as if recited in full herein.

In a second step, indanylidene compounds of the general formulae Ib, Ic and Id

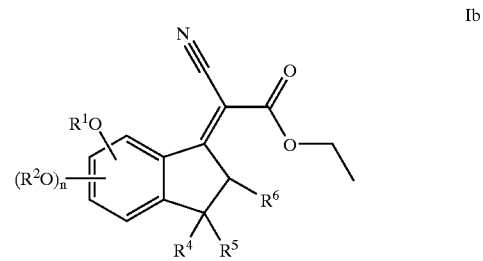

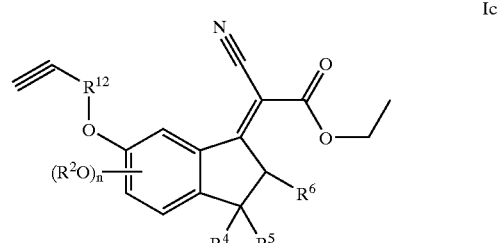

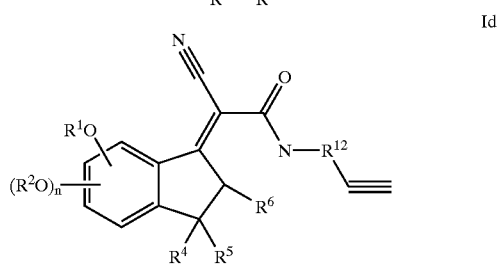

wherein $R^1$, $R^2$, $R^4$, $R^5$, $R^6$ and n are as defined above and $R^{12}$ is a $C_3$–$C_{12}$ divalent alkylene- or alkenylene chain are synthesized according to known reactions such as the Knoevenagel reaction. As stated above the $C_3$–$C_{12}$ divalent alkylene- or alkenylene chain may be interrupted by one or several oxygen atoms.

An example synthesis of an indanylidene compound of formula Ib is set forth below for a compound wherein $R^1$ and $R^2$ are methyl, n is 1, $R^4$ and $R^5$ are methyl, $R^6$ is hydrogen and X is oxygen. The corresponding compounds wherein $R^1$, $R^2$, $R^4$, $R^5$, $R^6$ and n are as defined above may be prepared accordingly. The details are described in Example 1.

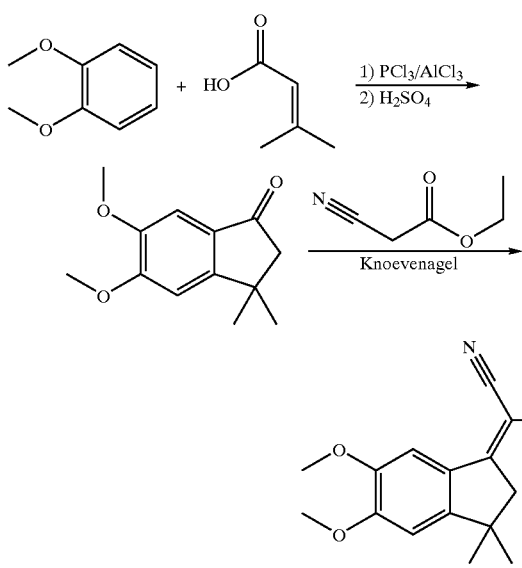

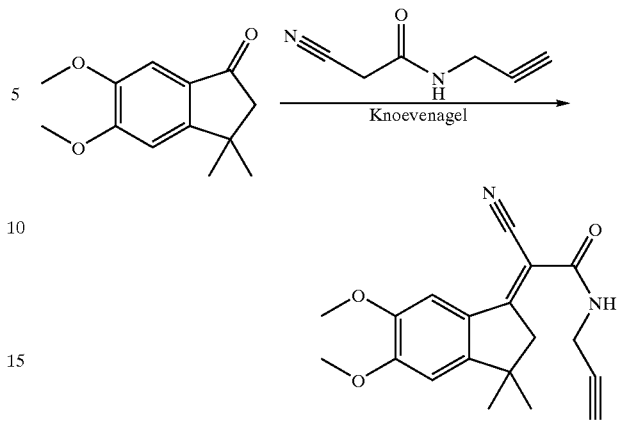

An example synthesis of an indanylidene compound of formula Ic is set forth below for a compound wherein $R^2$ is methyl, n is 1, $R^4$ and $R^5$ are methyl, $R^6$ is hydrogen and X is oxygen. The corresponding compounds wherein $R^2$, $R^4$, $R^5$, $R^6$ and n are as defined above may be prepared accordingly. The details are described in Examples 11a and 11b.

In a third step the indanylidene compounds of formulae Ib, Ic and Id are linked to the group YS according to known reactions either via a transesterification or a hydrosilation reaction.

An example of a transesterification reaction is set forth below for the reaction between a compound of formula Ib wherein X is oxygen, $R^1$ and $R^2$ are methyl, n is 1, $R^4$ and $R^5$ are methyl, $R^6$ is hydrogen and a compound ZYS, wherein Z is hydroxy, Y is 4-butyl and S is an oligosiloxane of formula IIa wherein $R^{10}$ is methyl and r is 1. The details of the reaction are described in Example 2. The corresponding compounds of formula I, wherein X is oxygen, e.g. Examples 3–7, may be prepared accordingly.

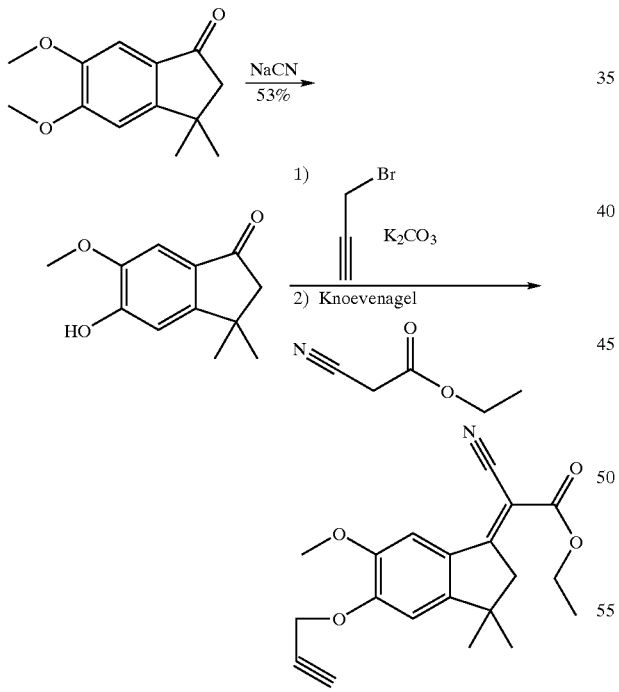

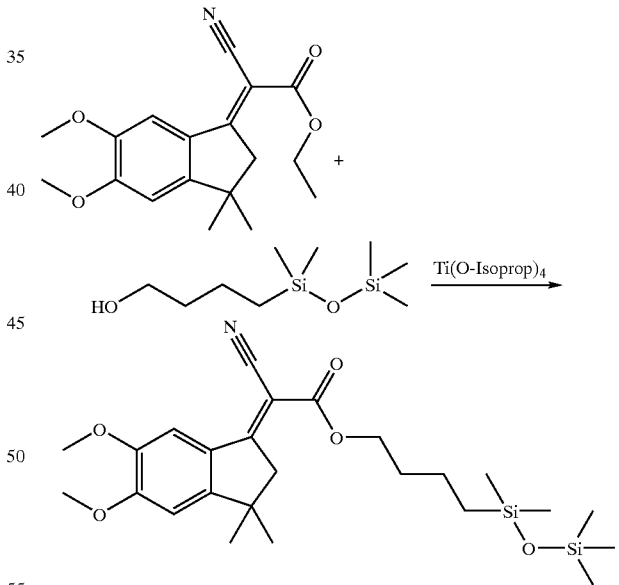

An example synthesis of an indanylidene compound of formula Id is set forth below for a compound wherein $R^1$ and $R^2$ are methyl, n is 1, $R^4$ and $R^5$ are methyl, $R^6$ is hydrogen and X is nitrogen. The corresponding compounds wherein $R^1$, $R^2$, $R^4$, $R^5$, $R^6$ and n are as defined above may be prepared accordingly. The details are described in Examples 8a and 8b.

In the hydrosilation reaction, compounds of formulae Ic and Id are reacted with a SiH containing oligosiloxane- or a polysiloxane compound corresponding to the oligosiloxane- or polysiloxane residues as defined above.

Two examples for a hydrosilation reaction are set forth below for the reaction between a compound of formula Id and a SiH containing oligosiloxane and a polysiloxane compound, respectively. The details of this reaction are set forth in Examples 8, 9, and 10. The corresponding compounds of the general formula I wherein X is nitrogen and $R^3$ is YS may be prepared accordingly.

a) Hydrosilation according to Example 8

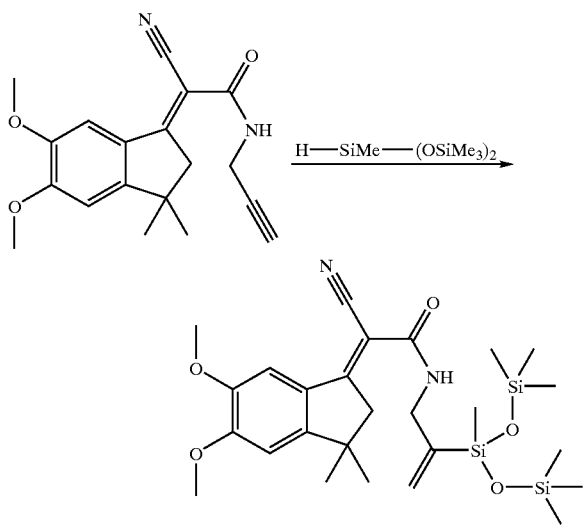

b) Hydrosilation according to Example 9

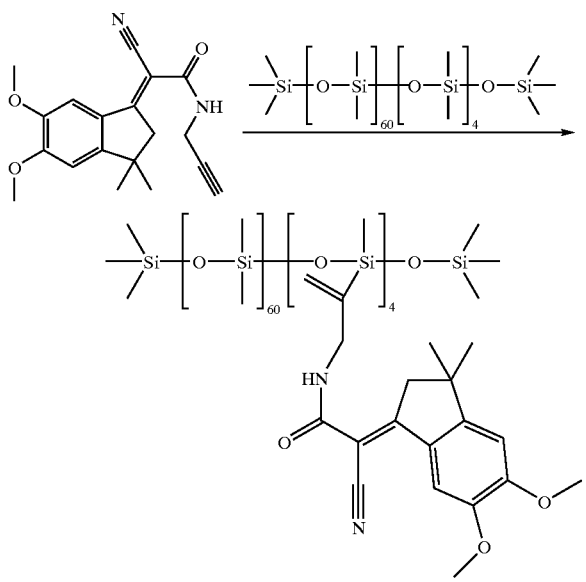

Examples 11 and 12 of the present invention set forth a hydrolisation reaction between a compound of formula Ic and a SiH containing oligosiloxane- and a polysiloxane compound, respectively. Compounds of formula I wherein X is nitrogen and $R^1$ is YS may be prepared accordingly.

The preparation of novel light screening agents, especially of preparations for skin protection and, respectively, sunscreen preparations for everyday cosmetics, includes incorporating a compound of formula I into a cosmetic base typically used for light screening agents. Other conventional UV-A and UV-B filters may also be combined during this incorporation. The combination of UV filters may lead to a synergistic light screening effect. The preparation of such light screening agents is well known to the skilled artisan in this field. In these light screening agents, the amount of compounds of formula I and other known UV-filters is not critical. Suitable amounts are about 0.5 to about 12%.

As used herein, suitable "UV B filters," include those substances having absorption maxima between about 290 and 320 nm. TVB filters include, for example, the following organic compounds, including but not limited to, for example:

p-Aminobenzoic acid derivatives such as, for example, ethyl, propyl, butyl, isobutyl, octyldimethyl, amyldimethyl, ethoxylated ethyl, propoxylated ethylglyceryl or ethylglycosyl p-aminobenzoate and the like;

Acrylates, such as, for example, 2-ethylhexyl 2-cyano-3, 3-diphenylacrylate (octocrylene), ethyl 2-cyano-3,3-diphenylacrylate and the like;

Aniline derivatives such as, for example, methyl anilinum methosulfate and the like;

Anthranilic acid derivatives such as, for example, menthyl anthranilate and the like;

Benzophenone derivatives such as, for example, benzophenone-1 to benzophenone-12 and the like.

Camphor derivatives such as, for example, methyl benzylidene camphor, 3-benzylidene camphor, camphor benzalkonium methosulfate, polyacrylamidomethyl benzylidene camphor, sulfo benzylidene camphor, sulfomethylbenzylidene camphor, therephthalidene dicamphor sulfonic acid and the like;

Cinnamate derivatives such as, for example, octyl methoxycinnamate or ethoxyethyl methoxycinnamate, diethanolamine methoxycinnamate, isoamyl methoxycinnamate and the like as well as cinnamic acid derivatives bond to siloxanes;

Gallic acid such as, for example, digalloyl trioleate and the like;

Imidazole derivatives such as, for example, phenyl benzimidazole sulfonic acid and their salts;

Salicylate derivatives such as, for example, isopropylbenzyl, benzyl, butyl, octyl, isooctyl or homomenthyl salicylate and the like;

Triazole derivatives such as, for example, drometriazole, hydroxydibutylphenyl-, hydroxydiamylphenyl-, hydroxyoctylphenyl- or hydroxyphenylbenztriazole and the like;

Triazone derivatives such as, for example, octyl triazone, dioctyl butamidotriazone and the like; and Pigments such as, for example, microparticulated $TiO_2$.

The formulation may further contain UV A filters such as, for example:

A Dibenzoylmethane derivative, such as, for example, 4-tert. butyl-4'-methoxydibenzoyl-methane and the like;

Pigments such as, for example, microparticulated ZnO.

Triazine compounds as described in EP 0693483 A1, EP 0704437 A2, EP 0704444 A1 and EP 0780382 A1;

Organosiloxane compounds as described in EP 0538431 B1, EP 0709080 A1 and EP 0358584B1; and Malonates such as, for example, those described in EP 895776 A2.

As used herein, the term "microparticulated" refers to a particle size from about 5 nm to about 200 nm, preferably from about 15 nm to about 100 nm.

The present invention includes cosmetic bases typically used for light screening compositions. Thus, such cosmetic bases include, for example, creams, lotions, emulsions, salves, gels, solutions, sprays, sticks and milks; see also, Sunscreens, Development, Evaluation and Regulatory Aspects, ed. N. Y. Lowe, N. A. Shaath, Marcel Dekker, Inc. New York and Basel, 1990, which is hereby incorporated by reference as if recited in full herein.

Having regard to their good lipophility, the compounds of formula I may be incorporated into oil-containing and fat-containing cosmetic preparations such as, for example, in cosmetic preparations containing dimethicone.

The following examples are provided to further illustrate methods of preparation of the compounds of the present invention, as well as certain physical properties and uses thereof. These examples are illustrative only and are not intended to limit the scope of the invention in any way.

EXAMPLES

Example 1

Synthesis of Cyano-(2,3-dihydro-5,6-dimethoxy-3,3-dimethyl-1H-inden-1-ylidene)acetic Acid Ethyl Ester

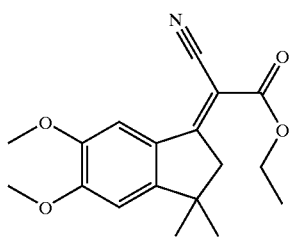

122 g (0.55 mol) of 2,3-Dihydro-5,6-dimethoxy-3,3-dimethyl-1H-inden-1-one (CAS N.[4136-26-9] for preparation see F. Camps, Z. Naturforsch., B : Anorg. Chem., Org. Chem. (1984), 39B (12), 1801–5), 63,3 g (0.56 mol) of ethyl cyano acetate, 12 g (0.14 mol of piperidine, 12 g (0.1 mol) of benzoic acid and 1000 ml toluene were mixed together and heated under reflux for 48 hours. The reaction mixture was cooled to room temperature, washed with diluted HCl, aqueous $Na_2CO_3$, and water and then dried ($MgSO_4$). Removal of the solvent and crystallization from EtOH gave 123.8 g of a yellow solid (m.p.: 148–149° C). Yield: 71%; $E^{1\%}_{cm}$: 790 (1 max.: 367 nm) in EtOH. Solubility: 0.35% in CÉTIOL LC

Example 2

Cyano-(2,3-dihydro-5,6-dimethoxy-3,3-dimethyl-1H-inden-1-ylidene) acetic Acid-3-(1,1,3,3,3-pentamethy-disiloxanyl)-propyl Ester

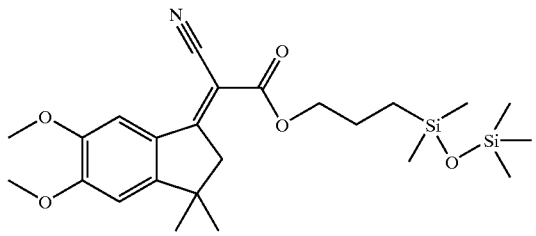

a) 3-(1,1,3,3,3-Pentamethy-disiloxanyl)-propanol

A 50 ml reaction flask was charged with 13.6 ml (200 mmol) of allylic alcohol and a catalytic amount of divinyl-tetramethyl disiloxane platinum complex under an inert atmosphere and heated to 60° C. 19.5 ml (100 mmol) of pentamethyl disiloxane was slowly added to the reaction flask through a dropping funnel. The exothermic reaction mixture was stirred overnight at 75° C., followed by a distillation at 105° C. to 107° C./40 to 41 mbar over a Vigreux column. The yield was 18.3 g (88.5% of the theory) of a clear liquid.

b) Transesterification

A 25 ml reaction flask equipped with a distillation bridge and connected to vacuum was charged with 2 g (6.3 mmol) of cyano-(2,3-dihydro-5,6-dimethoxy-3,3-dimethyl-1H-inden-1-ylidene) acetic acid ethyl ester (see Example 1), 1.37 g (6.6 mmol) of 3-(1,1,3,3,3-pentamethy-disiloxanyl)-propanol (see above) and 3 mg of tetraisopropyl ortho titanate. The mixture was heated to 115° C. to 120° C. at a vacuum of 360 mbar with stirring for 11 hours. The excess silylated alcohol was removed at 100° C./0.2 mbar and the residual product was chromatographed over $SiO_2$ in a hexane:ethylacetate solution (9.1 to 8:2) to yield 1.2 g (41%) of a liquid honey (m.p.: ca. 25° C.), UV 364 nm ($\epsilon$=26'093), which showed excellent solubility in cosmetic solvents such as >20% in CÉTIOL LC (Coco-caprylate/caprate) and was miscible in CRODAMOL DA (Diisopropyl adipate). The product showed an excellent photostability at high dilution of an ethanol solution using a Hg-1 amp 150 W from Heraeus with Pyrex filter.

Example 3

Cyano-(2,3-dihydro-5,6-dimethoxy-3,3-dimethyl-1H-inden-1-ylidene) acetic Acid-3-(1,1,3,3,3-pentamethy-disiloxanyl)-2-methyl-propyl Ester

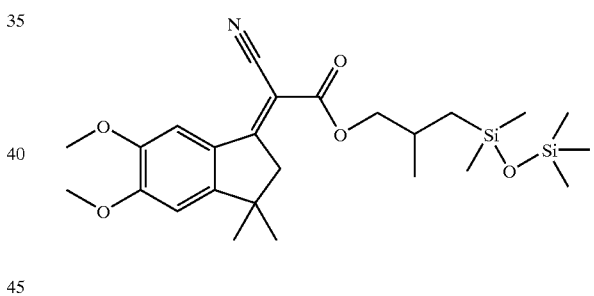

a) 3-(1,1,3,3,3 -Pentamethy-disiloxanyl)-2-methyl propanol

The reaction of Example 2a was repeated using 2-methallyl alcohol instead of allyl alcohol. After distillation at 105° C./40×10² Pa, 81% of a clear liquid product was obtained.

b) Transesterification

The reaction of Example 2b was repeated using 3-(1,1,3,3,3-pentamethy-disiloxanyl)-2-methyl propanol (see above) instead of 3-(1,1,3,3,3-pentamethy-disiloxanyl)-propanol. After 15 hours of reaction time, the product was concentrated and chromatographed as set forth above to yield 57% of a liquid material. UV 364 nm ($\epsilon$=25'200), having the same solubility and photostability qualities as described in Example 2b.

Example 4

Cyano-(2,3-dihydro-5,6-dimethoxy-3,3-dimethyl-1H-inden-1-ylidene) acetic Acid-4-(1,3,3,3-tetramethyl-1-[(trimethyl silyl)-oxy]-disiloxanyl)-butyl Ester

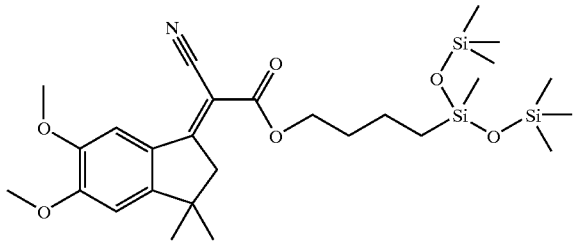

a) 4-(1,3,3,3-Tetramethyl-1-[(trimethyl silyl)-oxy]-disiloxanyl)-butanol

The reaction of Example 2a was repeated using 1,1,1,3,5,5,5-heptamethyl trisiloxane instead of 1,1,3,3,3-pentamethyl disiloxane and 3-butenol instead of allylalcohol. After distillation at 78° C./0.1×10² Pa, 83% of a clear liquid product was obtained.

b) Transesterification

A 25 ml reaction flask equipped with a distillation bridge and connected to vacuum was charged with 1.67 g (5.3 mmol) of Cyano-(2,3-dihydro-5,6-dimethoxy-3,3-dimethyl-1H-inden-1-ylidene) acetic acid ethyl ester (see example 1), 1.64 g (5.6 mmol) of 4-(1,3,3,3-tetramethyl-1-[(trimethyl silyl)-oxy]-disiloxanyl)-butanol (see above) and 3 mg of tetraisopropyl ortho titanate. The mixture was heated to 125° C. at a vacuum of 270 mbar under stirring for 9 hours. The excess silylated alcohol was removed at 0.2 mbar and the residual product was chromatographed over SiO₂ in a hexane:ethylacetate solution (9.1 to 7:3) to yield 2.3 g (78%) of a liquid, UV 364 nm (ε=25 '800) and 376 nm (ε=25'180). The product was miscible in CÉTIOL LC and CRODAMOL DA and showed an excellent photostability at high dilution in an ethanol solution using a Hg-1 amp 150 W from Heraeus with Pyrex filter.

Example 5

Cyano-(2,3-dihydro-5,6-dimethoxy-3,3-dimethyl-1H-inden-1-ylidene) acetic Acid-4-(2-triethylsilanyl-ethoxy)-butyl Ester

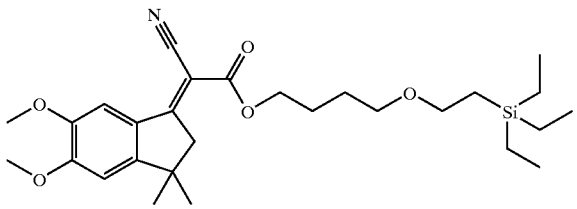

a) 4-(2-Triethylsilanyl-ethoxy)-butanol

A 50 ml reaction flask was charged with 11.6 ml (100 mmol) of 1,4-butandiol-mono vinylether and a catalytic amount of divinyl-tetramethyl disiloxane platinum complex under inert atmosphere and heated to 60° C. 10.4 g (90 mmol) of triethylsilane was slowly added to the reaction flask through a dropping funnel. The exothermic reaction mixture was stirred at 75° C. for 18 hours, followed by distillation at 105° C. to 107° C./0.2 mbar over a 10 cm Vigreux column. This reaction yielded 15.2 g (66% of the theory) of a clear liquid. Purity according to gas chromatography was 98.7%.

b) Transesterification

The reaction of Example 2b was repeated using 4-(2-triethylsilanyl-ethoxy)-butanol (see above) instead of 3-(1,1,3,3,3-pentamethy-disiloxanyl)-propanol. After 8 hours reaction time, the product was concentrated and chromatographed as set forth above to yield 70% of a liquid material. UV 364 nm (ε=27'126). The product had the same solubility and photostability qualities as described in Example 2b.

Example 6

Cyano-(2,3-dihydro-5,6-dimethoxy-3,3-dimethyl-1H-inden-1-ylidene) acetic Acid-4-triethylsilanyl-but-3-enyl Ester

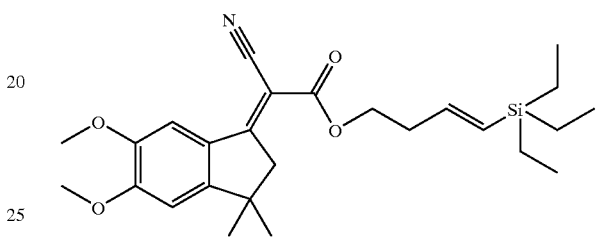

a) 4-Triethylsilanyl-1-but-3-enol

A 50 ml reaction flask was charged with 1-butyne-3-ol and a catalytic amount of bis(1,5-cyclooctadiene)-di-Rh(I)-dichloride and triphenylphosphine under an inert atmosphere. Triethylsilane was slowly added to the reaction flask through a dropping funnel. The reaction mixture was stirred at room temperature for 72 hours and then concentrated at the rotary evaporator. The product was chromatographed through SiO₂ in a hexane:ethylacetate solution (95:5 to 70:30) to yield 86% of a yellow liquid. Purity according to gas chromatography was 96% trans and 3.4% cis product.

b) Transesterification

The reaction of Example 2b was repeated using 4-triethylsilanyl-1-but-3-enol (see above) instead of 3-(1,1,3,3,3-pentamethy-disiloxanyl)-propanol. After 9 hours of reaction time, the product was concentrated and chromatographed as set forth above to yield 65% of a semi-crystalline material. UV 368 nm (ε=26'748). The product had the same solubility and photostability qualities as described in Example 2b

Example 7

Cyano-(2,3-dihydro-5-methoxy-2-methyl-1H-inden-1-ylidene)acetic Acid-4-(1,1,3,3,3-pentamethy-disiloxanyl)-butyl Ester

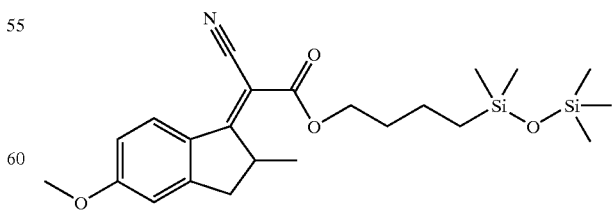

a) 4-(1,1,3,3,3-Pentamethy-disiloxanyl)-butanol
b) A 50 ml reaction flask was charged with 10.3 ml of 3-butene-1-ol and a catalytic amount of divinyl-tetramethyl disiloxane platinum complex under inert atmosphere and heated to 60° C. 19.5 ml of pentamethyl disiloxane was slowly added to the reaction flask through a dropping funnel. The reaction mixture was stirred at 75° C. to 80° C. for three hours, followed by distillation at 110° C. to 115° C./38×10$^2$ Pa over a 10 cm column. The yield was 18.9 g (86% of the theory) of a clear liquid.

c) 2,3-Dihydro-5-methoxy-2-methyl-1H-inden-1-one

5-Methoxy indanone was treated with aqueous formaldehyde in the presence of iron pentacarbonyl and KOH in ethanol according to G. Cainelli et. al., *Tetrahedron Letters* 27, 2491 (1973). After chromatography (hexane:ethylacetate=7:3) over SiO$_2$, a 44% yield of white crystals was obtained (m.p. 73–76° C.).

d) Cyano-(2,3-dihydro-5-methoxy-2-methyl-1H-inden-1-ylidene)acetic Acid 2-ethyl-hexyl Ester The above 2,3-dihydro-5-methoxy-2-methyl-1H-inden-1-one (5.2 g) was reacted with 5.9 g of 2-ethyl-hexyl cyano acetate in the presence of catalytic amounts of pyrrolidine and benzoic acid in 100 ml of toluene. The reaction mixture was refluxed for 30 hours with simultaneous separation of water. Then, the cold reaction mixture was washed with water, concentrated and chromatographed in toluene containing 2% of propanol through SiO$_2$ to yield 2.6 g of a yellow liquid. UV 347 nm ($\epsilon$=33'450), MS: 355(M$^+$), 243 (100%), 226, 198.

e) Transesterification

The reaction of Example 2b was repeated using 4-(1,1,3,3,3-pentamethy-disiloxanyl)-butanol (see above) instead of 3-(1,1,3,3,3-pentamethy-disiloxanyl)-propanol as well as the above cyano-(2,3-dihydro-5-methoxy-2-methyl-1H-inden-1-ylidene)acetic acid 2-ethyl-hexyl ester instead of the product of example 1. After 9 hours of reaction time, the product was concentrated and then treated for another 5 hours as set forth above with new 3-(1,1,3,3,3-pentamethy-disiloxanyl)-propanol. The mixture was then concentrated and chromatographed as before to yield 30% of a liquid material. UV 347 nm ($\epsilon$=32'500). This product had the same solubility and photostability qualities as described in Example 2b.

Example 8

Cyano-(2,3-dihydro-5,6-dimethoxy-3,3-dimethyl-1H-inden-1-ylidene)acetic Acid-2-(1,3,3,3-tetramethyl-1-[(trimethylsilyl)-oxy]-disiloxanyl)-prop-2-enyl Amide

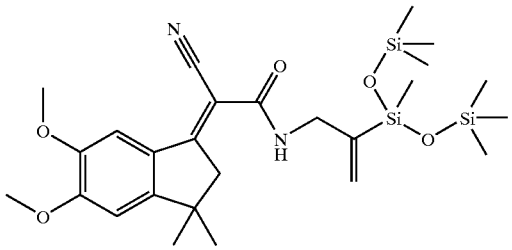

a) 2-Cyano-N-prop-2-ynyl-acetamide

A mixture of 15.4 ml (240 mmol) of propargyl amine and 17.1 ml (160 mmol) of ethyl cyano acetate was heated for 7 hours to 40° C. in a reaction flask. The crystalline material formed was heated for another 17 hours to 70° C. Then, the cooled reddish product was dried at high vacuum to yield 18.4 g (94%) of a red powder, m.p. 100–103° C.

b) 2-Cyano-2-(5,6-dimethoxy-3,3-dimethyl-indan-1-ylidene)-N-prop-2-ynyl-acetamide A 50 ml reaction flask equipped with a water separator and a reflux condenser was charged with 2.2 g of 2,3-dihydro-5,6-dimethoxy-3,3-dimethyl-1H-inden-1-one (see Example 1), 1.2 g of 2-cyano-N-prop-2-ynyl-acetamide (see above), catalytic amounts of pyrrolidine, and benzoic acid in 20 ml of toluene. The reaction mixture was refluxed for 24 hours with simultaneous separation of water. Then, the product in the cold reaction mixture was filtered off and recrystallized in ethylacetate to yield 1.13 g of white crystals, m.p. 202° C.–205° C. UV 362 nm ($\epsilon$=24'992). Solubility: 0.04% in CÉTIOL LC c) Hydrosilylation Reaction The above 2-cyano-2-(5,6-dimethoxy-3,3-dimethyl-indan-1-ylidene)-N-prop-2-ynyl-acetamide (320 mg), 220 mg of 1,1,1,3,5,5,5-heptamethyl trisiloxane and a catalytic amount of divinyl-tetramethyl disiloxane platinum complex in 10 ml of toluene was placed in a three-necked reaction flask under an inert atmosphere and stirred for 48 hours at 95° C. The product solution was washed with a mixture of water/methanol=1:10 and concentrated to yield 550 mg (100%) of a yellow liquid. UV 360 nm ($\epsilon$=22'069), MS: 546 (M$^+$), 531, 299, 270, 269 (100%). The NMR of the product showed a mixture of the vicinal and the geminal hydrosilylation product of 1:2. The product was miscible in CÉTIOL LC and CRODAMOL DA and showed the same photostability qualities as described in Example 2b.

Example 9

A polysiloxane which Corresponds in its Statistical Mean Value to the Following Formula:

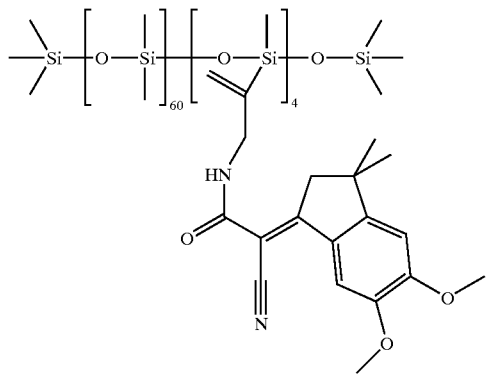

2-Cyano-2-(5,6-dimethoxy-3,3-dimethyl-indan-1-ylidene)-N-prop-2-ynyl-acetamide (320 mg), 1180 mg of polysiloxane Ae-151 (from Wacker-Chemie GmbH), and a catalytic amount of divinyl-tetramethyl disiloxane platinum complex in 10 ml of toluene was placed in a three-necked reaction flask under an inert atmosphere and heated for 48 hours to 95° C. The product solution was washed with a mixture of water/methanol=1:10 and concentrated to yield 1500 mg (100%) of a yellow liquid. UV 360 nm (E=210.6). The product was miscible in CÉTIOL LC and CRODAMOL DA and showed the same photostability qualities as described in Example 2b.

Example 10

α-(Dimethyl-[2N-[2-cyano-2-(5,6-dimethoxy-3,3-dimethyl-indan-1-ylidene)-acetamide]-1-methylene-ethyl]-ω-(dimethyl-[2N-[2-cyano-2-(5,6-dimethoxy-3,3-dimethyl-indan-1-ylidene)-acetamide]-1-methylene-ethyl]-poly-(oxy-(dimethyl)-silene), n~9

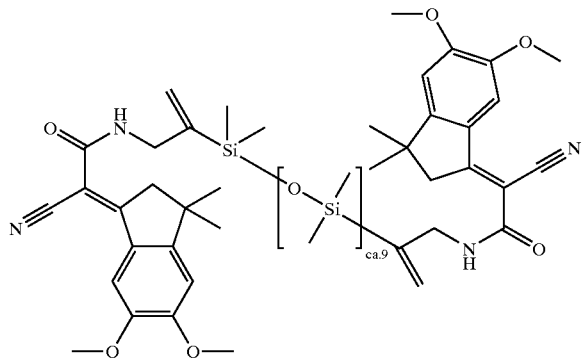

2-Cyano-2-(5,6-dimethoxy-3,3-dimethyl-indan-1-ylidene)-N-prop-2-ynyl-acetamide (320 mg), 340 mg of polysiloxane VP-1085 (from Wacker-Chemie GmbH), and a catalytic amount of Pt on charcoal 5% in 10 ml of toluene was placed in a three-necked reaction flask under an inert atmosphere and heated for 44 hours to 105° C. The product solution was filtered through Cellite, washed with a mixture of water/methanol=1:10 and concentrated to yield 560 mg (85%) of a yellow liquid. UV 360 nm (E=329). The product was miscible in CÉTIOL LC and CRODAMOL DA and showed the same photostability qualities as described in Example 2b.

Example 11

Cyano-(6-methoxy-3,3-dimethyl-5-[2-((1,3,3,3-tetramethyl-1-[(trimethyl silyl)-oxy]-disiloxanyl)-allyloxy]-indan-1-ylidene)-acetic Acid Ethyl Ester

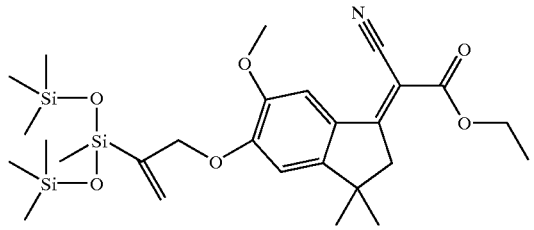

a) 6-Methoxy-3,3-dimethyl-5-hydroxy-indan-1-one

In a three necked reaction flask equipped with a reflux condenser, a mixture of 5 g of 2,3-dihydro-5,6-dimethoxy-3,3-dimethyl-1H-inden-1-one (see example 1) and 5.5 g of sodium cyanide in 44.5 ml of dimethyl formamide was stirred at 100° C. for 40 hours. Then, the mixture was pored on an aqueous NaH$_2$PO$_4$ solution and extracted 4 times with ethyl acetate, dried over Na$_2$CO$_3$, and concentrated. The raw product was chromatographed in methylene chloride containing 1% of methanol to yield 2.5 g of white crystals. m.p. 105–107° C. MS: 206(M$^+$), 191(100%), 163, 131, 103.

b) 6-Methoxy-3,3-dimethyl-5-prop-2-ynyloxy-indan-1-one

6-Methoxy-3,3-dimethyl-5-hydroxy-indan-1-one (2.2 g), 1.5 g of propargyl bromide, and 3.7 g of K$_2$CO$_3$ in 9 ml of 1-methyl pyrrolidone was placed in a 25 ml reaction flask and stirred for one hour. Then, it was stirred further at 100° C. for one hour. The reaction mixture was distributed between water and ethyl acetate. The organic phase was washed with 1N NaOH solution and NaCl solution, dried over Na$_2$SO$_4$ and concentrated to yield 2.7 g of a yellow liquid. UV 310 nm (ε=18'734), MS: 244(M$^+$), 229, 105 (100%).

c) Cyano-(6-methoxy-3,3-dimethyl-5-prop-2-ynyloxy-indan-1-ylidene)-acetic Acid Ethyl Ester The above 6-methoxy-3,3-dimethyl-5-prop-2-ynyloxy-indan-1-one (2.44 g) was treated with 1.13 g of ethyl cyano acetate in the presence of 0.1 equivalents of pyrrolidine and benzoic acid in 20 ml of xylene. The reaction mixture was refluxed for 30 hours with simultaneous separation of water. Then, the cold reaction mixture was washed with water, concentrated and chromatographed in hexane/ethyl acetate through SiO$_2$ to yield 0.7 g of yellow crystals. m.p. 132–136° C. UV 362 nm (ε=23'222), MS: 339(M$^+$), 324, 300 (100%).

d) Hydrosilylation Reaction

Cyano-(6-methoxy-3,3-dimethyl-5-prop-2-ynyloxy-indan-1-ylidene)-acetic acid ethyl ester (500 mg), 330 mg of 1,1,1,3,5,5,5-heptamethyl trisiloxane, and a catalytic amount of divinyl-tetramethyl disiloxane platinum complex in 15 ml of toluene was placed in a three-necked reaction flask under an inert atmosphere and heated for 24 hours to 78° C. The product solution was concentrated and filtered through SiO$_2$ in hexane/ethyl acetate=9:1 and again concentrated to yield 590 mg (71%) of a yellow liquid. UV 367 nm (ε=23'515), MS: 561(M$^+$), 546, 509(100%). The NMR of the product shows a mixture of the vicinal and the geminal hydrosilylation product of 2:1. The product was miscible in CÉTIOL LC and CRODAMOL DA and showed the same photostability qualities as described in Example 2b.

Example 12

A Polysiloxane which Corresponds in its Statistical Mean Value to the Following Formula:

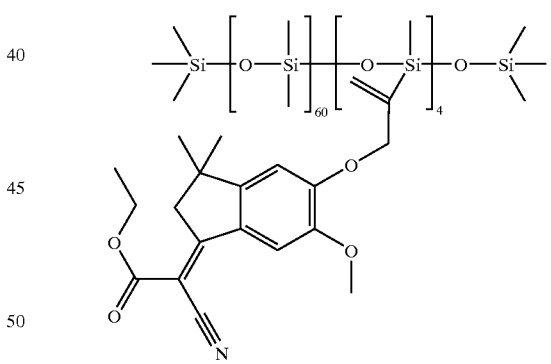

Cyano-(6-methoxy-3,3-dimethyl-5-prop-2-ynyloxy-indan-1-ylidene)-acetic acid ethyl ester (280 mg), 770 mg of polysiloxane Ae-151 (from Wacker-Chemie GmbH), and a catalytic amount of divinyl-tetramethyl disiloxane platinum complex in 10 ml of toluene was placed in a three-necked reaction flask under inert atmosphere and heated for 20 hours to 80° C. The product solution was washed with a mixture of water/methanol=1:10, concentrated and filtered through SiO$_2$ to yield 1100 mg (100%) of a yellow liquid. UV 366 nm (ε=26'172/E=180.5). The NMR of the product shows both vicinal and geminal hydrosilylation product. The product was miscible in CÉTIOL LC and CRODAMOL DA and showed the same photostability qualities as described in Example 2b.

Example 13

A Polysiloxane which Corresponds in its Statistical Mean Value to the Following Formula

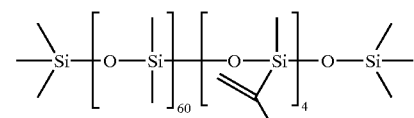

In a first step, 5-methoxy-3,3-dimethyl-6-prop-2-ynyloxy-indan-1-one was prepared as follows:

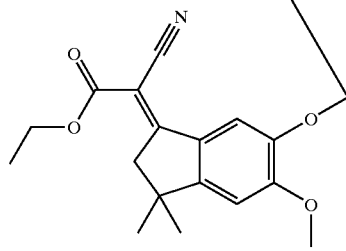

45.8 g of 5-methoxy-3,3-dimethyl-6-hydroxy-indan-1-one (CAS N.(98910-58-8)), 24.4 g of propargyl chloride, and 8.9 g of NaH in 300 ml of DMF were stirred for one hour at room temperature and then heated for 20 hours at 50° C. The reaction mixture was distributed between water and toluene. The organic phase was washed with $Na_2CO_3$ and water, dried over $Na_2SO_4$ and concentrated to yield 41.7 g of a brown liquid. $^1$H-NMR (200 MHz): 1.41 (s, 6H); 2.52–2.58 (m, 3H); 3.99 (s, 3H); 4.79 (d, J=2 Hz, 2H); 6.89 (s, 1H); 7.27 (s, 1H).

To prepare cyano-(5-methoxy-3,3-dimethyl-6-prop-2-ynyloxy-indan-1-ylidene)-acetic acid ethyl ester

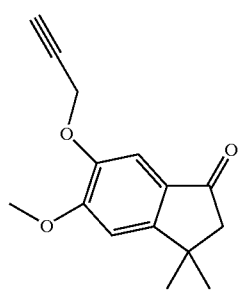

41.7 g of the above 5-methoxy-3,3-dimethyl-6-prop-2-ynyloxy-indan-1-one was treated with 21.49 g of ethyl cyano acetate in the presence of 16 g of piperidine, and 16 g of benzoic acid in 1300 ml of cyclohexane. The reaction mixture was refluxed for 24 hours with simultaneous separation of water. Then, the cold reaction mixture was washed with water, HCl 1%, $Na_2CO_3$, and water. The reaction mixture was concentrated and recrystallized in EtOH to yield 24.3 g of yellow crystals: $^1$H-NMR (200 MHz): 1.33 (s, 6H); 1.38 (t, J=7Hz, 3H); 2.57 (t, J=2 Hz, 1H); 3.37 (s, 3H); 3.99 (s, 3H); 4.31 (q, J=7 Hz, 2H); 4.83 (d, J=2 Hz, 2H); 6.80 (s, 1H); 8.26 (s, 1H).

α-(Trimethylsilyl)-ω-(trimethylsilyl-oxy)-poly-(oxy-(dimethyl)- and about 7.5% of methyl-(6-[-1-cyano-ethyloxy-acetyl-(5-methoxy-3,3-dimethyl-indan-1-ylidene]-1-methylene-eth-2-oxy)-silene):

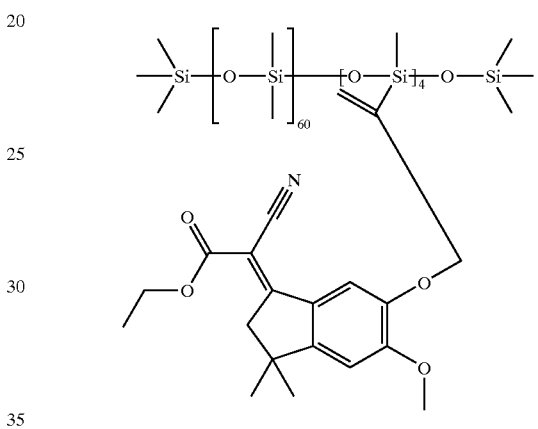

16.13 g of the above Cyano-(5-methoxy-3,3-dimethyl-6-prop-2-ynyloxy-indan-1-ylidene)-acetic acid ethyl ester, 54.95 g of polysiloxane Ae-151 (from Wacker-Chemie GmbH), and a catalytic amount of Pt/C (Heraeus type k-0101) in 75 ml of toluene were heated for 28 hours at 110° C. The reaction mixture was filtrated and then washed with a mixture of water/methanol=1:5, concentrated to give 67.8 g a yellow liquid. UV 368 nm (E=150). The NMR of the product showed both vicinal and geminal hydrosilylation product. The product was miscible in CÉTIOL LC and CRODAMOL DA and showed the same photostability qualities as described in Example 2b.

Solubility

The compounds of formula I have excellent solubility in cosmetic solvents. The compounds of Examples 2 to 12 are miscible in CRODAMOL DA. The solubility in CÉTIOL LC is >20% for compounds of Examples 2, 3, 5, and 6. Examples 4 and 8–12 are miscible in CÉTIOL LC Table 1 below contains solubility data of indanylidene compounds disclosed in EP 0823 418 A2 and of compounds according to the present invention.

TABLE 1
| Compound | Solubility in CÉTIOL LC | Solubility in CRODAMOL DA |
|---|---|---|
| 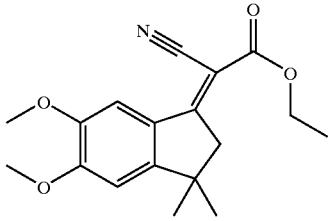 | 0.35% | 1.71% |
| 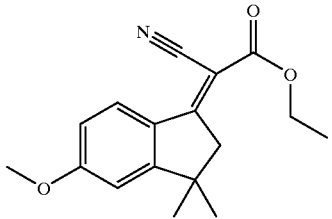 | 0.10% | 0.60% |
| 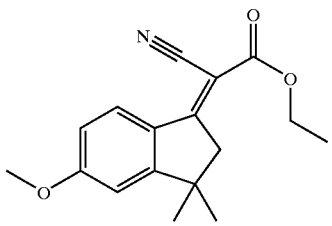 | 0.09% | — |
| 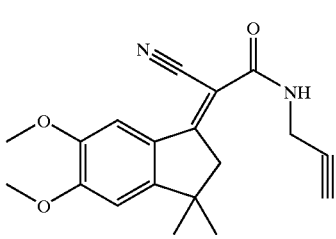 | 0.04% | — |
| 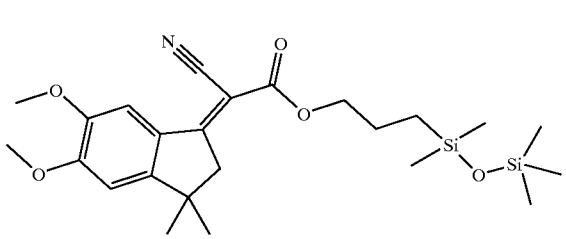 | >20% | miscible |
| 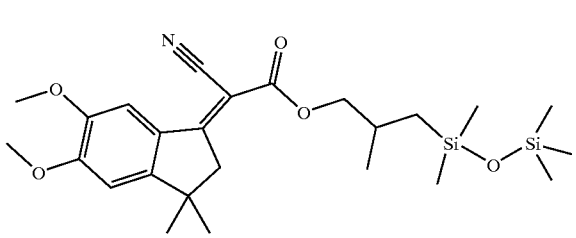 | >20% | miscible |

TABLE 1-continued
| Compound | Solubility in CÉTIOL LC | Solubility in CRODAMOL DA |
|---|---|---|
| 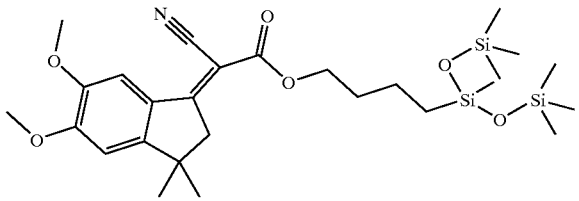 | miscible | miscible |
| 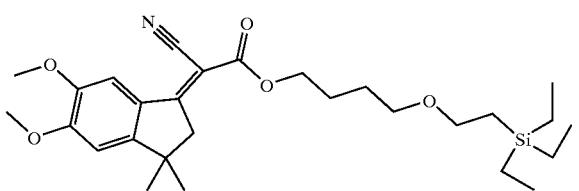 | >20% | miscible |
| 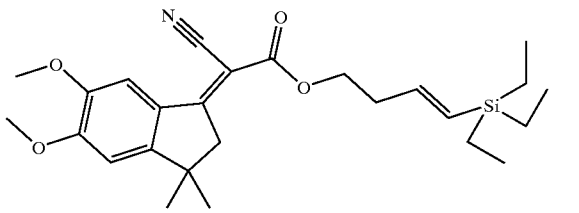 | >20% | miscible |
| 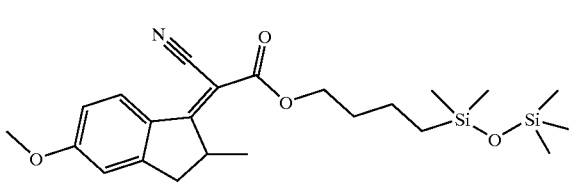 | miscible | miscible |
| 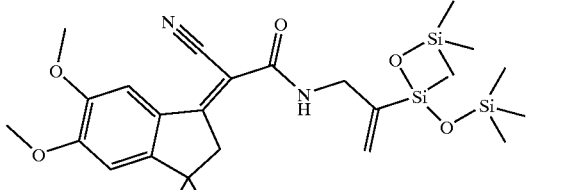 | miscible | miscible |
| 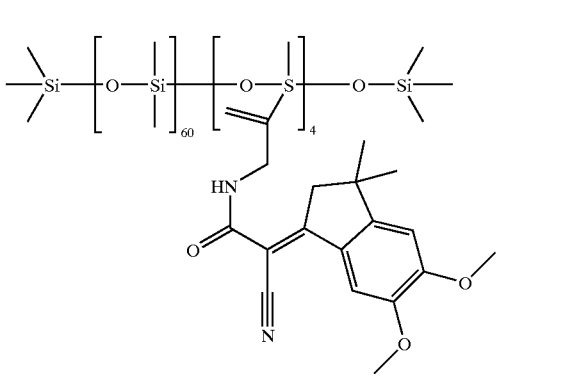 | miscible | miscible |

TABLE 1-continued

| Compound | Solubility in CÉTIOL LC | Solubility in CRODAMOL DA |
|---|---|---|
| 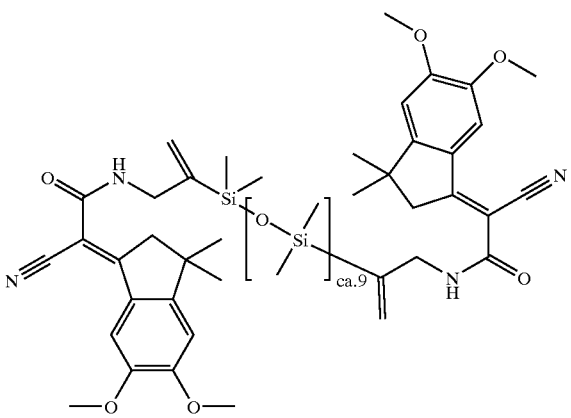 | miscible | miscible |
| 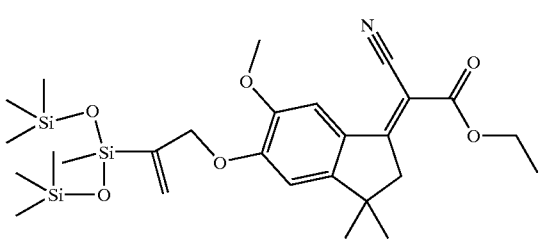 | miscible | miscible |
| 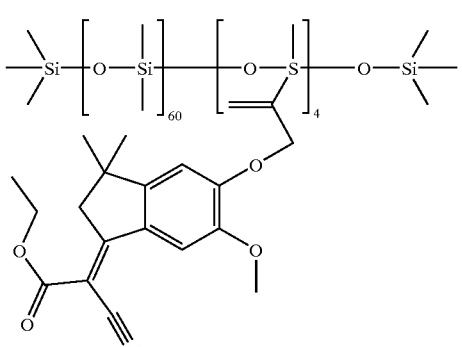 | miscible | miscible |
| 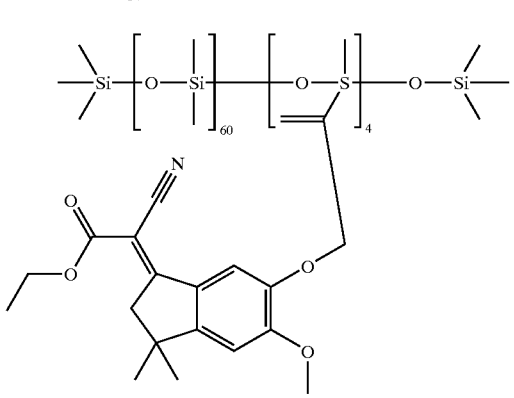 | miscible | miscible |

The following Examples 14–16 illustrate light screening agents provided by the present invention. In these examples, the trade names selected have the following meanings:

AMPHISOL DEA: Diethanolamine cetylphosphate sold under the tradename AMPHISOL DEA by Givaudan Roure S. A, F-95101 Argenteuil-Paris.

CARBOPOL 934: Carbomer sold under the tradename CARBOPOL 934 by B. F. Goodrich Company, Brecksville, Ohio 44141, USA.

CERAPHYL 375: Isostearyl neopentanoate sold under the tradename CERAPHYL 375 by ISP Global Technologies Deutschland GmbH, Frechen, Germany.

CERAPHYL 847: Octyldodecyl stearoyl stearate sold under the tradename CERAPHYL 847 by ISP.

CETIOL LC: Coco-caprylate/caprate sold under the tradename CETIOL LC by Henkel KgA, Düsseldorf, Germany.

CRODAMOL DA: Diisopropyladipate sold under the tradename CRODAMOL DA by Croda.

DERMOL 185: Isostearyl neopentanoate sold under the tradename DERMOL 185 by Bernel.

EDETA BD: Disodium EDTA sold under the tradename EDETA BD by BASF A G, Ludwigshafen, Germany.

ESTOL GTEH 3609: Trioctanoin sold under the trade name ESTOL GTEH 3609 by Unichema Chemie GmbH, Emmerich, Germany.

ESTOL GMM 3650: Glyceryl Myristate sold under the trade name ESTOL GMM 3650 by Unichema.

GANEX V-220: PVP/Eicosene copolymer sold under the tradename GANEX V-220 by ISP.

NIPAGIN M: Methylparaben sold under the tradename NIPAGIN M by Nipa Lab. Ltd., Pontypridd Mid Glam, Wales/GB PARSOL MCX: Octyl methoxycinnamate sold under the tradename PARSOL MCX by F. Hoffmann-la Roche Ltd, CH-4070 Basel.

PARSOL 1789: 4-t-Butyl-4'-methoxy-dibenzoyl-methane sold under the trade name PARSOL 1789 by Roche.

PARSOL 5000: 4-Methylbenzylidene camphor sold under the tradename PARSOL 5000 by Roche.

PHENONIP: Phenoxyethanol & Methyl-, Ethyl-, Propyl- & Butyl-paraben sold under the tradename PHENONIP by Nipa T-COTE 031: Titanium Dioxide & Dimethicone sold under the tradename T-COTE 031 by Sunsmart, Wainscott-N.Y. 11975, USA Example 14

Preparation of a O/W Broad Spectrum Sunscreen Lotion Containing 2% of the Product Described in Example 2

| % w/w | Ingredient | Chemical Name/INCI Name |
|---|---|---|
| Part A | | |
| 2.0 | PARSOL MCX | Octyl methoxycinnamate |
| 2.0 | Product of Example 2 | |
| 3.0 | PARSOL 1789 | 4-t-Butyl-4'-methoxy-dibenzoyl-methane |
| 12.0 | CETIOL LC | Coco-caprylate/caprate |
| 4.0 | DERMOL 185 | Isostearyl neopentanoate |
| 0.25 | Diethyleneglycol monostearate | PEG-2-stearate |
| 1.0 | Cetylalcohol | Cetylalcohol |
| 0.25 | MPOB/PPOB | Methyl-propylparabene |
| 0.1 | EDTA BD | EDTA-sodium salt |
| 1.0 | AMPHISOL DEA | Diethanolamine cetylphosphate |
| Part B | | |
| 20.0 | Permulene TR-1 (+%) | Acrylate C10–C30 Alkylacrylate |
| 48.6 | Deionized Water | Deionized Water |
| 5.0 | Propyleneglycol | 1,2-Propanediol |
| 0.8 | KOH (10%) | Potassium hydroxide |

Part A was heated in a reactor to 85° C. Part B was slowly added to Part A within 10 minutes, followed by addition of KOH, cooling and degassing of the emulsion.

Example 15

Preparation of an O/W (Oil in Water Emulsion) Anionic Broad Spectrum Sunscreen Lotion Containing 4% of the Product Described in Example 8

| % w/w | Ingredient | Chemical Name/INCI Name |
|---|---|---|
| Part A | | |
| 3.0 | PARSOL MCX | Octyl methoxycinnamate |
| 4.0 | Product of Example 8 | |
| 3.0 | PARSOL 5000 | 4-Methylbenzylidene camphor |
| 4.0 | PARSOL 1789 | 4-t-Butyl-4'-methoxy-dibenzoyl-methane |
| 2.0 | Glyceryl monostearate | Glyceryl stearate |
| 2.0 | Cetyl alcohol extra | Cetyl alcohol |
| 2.0 | GANEX V-220 | PVP/Eicosene copolymer |
| 4.0 | CERAPHYL 375 | Isostearyl neopentanoate |
| 4.0 | CERAPHYL 847 | Octyldodecyl stearoyl stearate |
| 2.0 | AMPHISOL K | Potassium cetylphosphate |
| 0.1 | EDETA BD | Disodium EDTA |
| 0.6 | PHENONIP | Phenoxyethanol & Methyl-, Ethyl-, Propyl- & Butyl-paraben |
| Part B | | |
| 11.2 | Deionized Water | Deionized Water |
| 50.0 | CARBOPOL 934 1% solution | Carbomer |
| 5.0 | Propyleneglycol | 1,2-Propanediol |
| 0.2 | NIPAGIN M | Methylparaben |
| 3.0 | KOH (10%) | Potassium hydroxide |
| q.s. | Perfume oil | Fragrance |

Part A was heated in a reactor to 85° C. When Part A became homogeneous, Part B was added, followed by addition of preheated KOH (75° C.), cooling and degassing of the emulsion.

Example 16

Preparation of an O/W (Oil in Water Emulsion) Broad Spectrum Sunscreen Cream with Pigments having Low Skin Penetration Quality and Containing 4% of the Product Set Forth in Example 9

| % w/w | Ingredients | Chemical Name/INCI Name |
|---|---|---|
| Part A | | |
| 8.0 | Polysiloxane A described in EP 0709080 A1 | Polysiloxane grafted benzalmalonate UV-B sunscreen |
| 4.0 | Product of Example 9 | |
| 6.0 | T-COTE 031 | Titanium Dioxide & Dimethicone |
| 10.0 | ESTOL GTEH 3609 | Trioctanoin |
| 1.0 | Cetyl Alcohol | Cetyl Alcohol |
| 4.0 | ESTOL GMM 3650 | Glyceryl Myristate |
| 0.05 | Butylated Hydroxytoluene | BHT |
| 0.1 | EDETA BD | Disodium EDTA |
| 0.6 | PHENONIP | Phenoxyethanol & Methylparaben & Ethylparaben & Propylparaben & Butylparaben |
| 2.0 | AMPHISOL K | Potassium Cetyl Phosphate |
| Part B | | |
| 50.8 | Deionized Water | Deionized Water |
| 10.0 | Carbopol 980 1% sol'n | Carbomer 980 |
| 3.0 | Glycerin | Glycerin |

| % w/w | Ingredients | Chemical Name/INCI Name |
|---|---|---|
| | | Part C |
| 0.5 | KOH 10% sol'n | Potassium Hydroxide |
| | | Part D |
| q.s. | Perfume Oil | Fragrance |

The components of Part A were heated to 85° C. while stirring. After mixing for 30 seconds with a turbine at 8000 t/minute, the components of Part B and Part C were added to the homogeneous mixture of Part A. The mixture was heated to 75° C., while stirring. After cooling to 40° C., the ingredients of Part D were added. The water loss was compensated and the mixture was cooled to room temperature under stirring followed by mixing for 30 seconds with a turbine at 8000 t/minute.

The invention being thus described, it will be obvious that the same may be varied in many ways. Such variations are not to be regarded as a departure from the spirit and scope of the invention and all such modifications are intended to be included within the scope of the following claims.

We claim:

1. A compound of formula I:

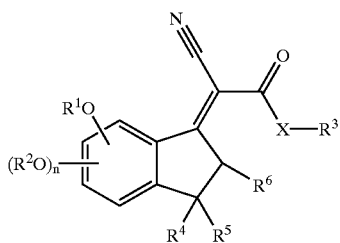

wherein
X is a O or NH;
$R^1$ is a $C_1$–$C_{20}$ alkyl, $C_2$–$C_{20}$ alkyl in which at least one methylene group is replaced by oxygen, $C_3$–$C_{20}$ alkenyl, $C_3$–$C_{20}$ alkynyl or a group YS;
$R^2$ is a $C_1$–$C_{20}$ alkyl, $C_2$–$C_{20}$ alkyl in which at least one methylene group is replaced by oxygen, $C_3$–$C_{20}$ alkenyl, $C_3$–$C_{20}$ alkynyl or a group YS; or $R^1$ and $R^2$ may combine on adjacent C-atoms to form a dioxomethylene ring;
$R^3$ is a $C_1$–$C_{20}$ alkyl, $C_2$–$C_{20}$ alkyl in which at least one methylene group is replaced by oxygen, $C_3$–$C_{20}$ alkenyl, $C_3$–$C_{20}$ alkynyl or a group YS;
$R^4$, $R^5$, $R^6$ are each independently H or $C_1$–$C_{20}$ alkyl;
n is 0, 1 or 2;
Y is a linker group;
S is a silane-, an oligosiloxane- or a polysiloxane- moiety; with the proviso that at least one of the residues $R^1$, $R^2$ or $R^3$ is YS.

2. A compound according to claim 1, wherein $R^2$ is selected from the group consisting of $C_1$–$C_{20}$ alkyl, $C_2$–$C_{20}$ alkyl in which at least one methylene group is replaced by oxygen, $C_3$–$C_{20}$ alkenyl, and $C_3$–$C_{20}$ alkynyl, or $R^1$ and $R^2$ may combine on adjacent C-atoms to form a dioxomethylene ring.

3. A compound according to claim 1 wherein the linker group is $C_3$–$C_{12}$ divalent alkylene, an alkenylene chain which links the silane, oligosiloxane or polysiloxane moiety to the UV absorbing chromophoric residue.

4. A compound according to claim 3 wherein the linker group is selected from the group consisting of 3-propylene, 2-propylene, 2-methyl-3-propylene, 3-butylene, 4-butylene, 4-pentylene, 5-pentylene, 6-hexylene, 2-propen-2-ylene, 2-propen-3-ylene, 3-buten-3-ylene, 3-buten-4-ylene, 4-penten-4-ylene, 4-penten-5-ylene, (3-methyl)-penta-2,4-dien-4 or 5-ylene, 11-dodecen-11-ylene, 2-ethyloxy-eth-2-ylene, 4-butyloxy-eth-2-ylene and 3,6-dioxa-8-octylene.

5. A compound according to claim 1 wherein S is —$SiR^7R^8R^9$ wherein $R^7$, $R^8$ and $R^9$ each independently are $C_1$–$C_6$ alkyl, $C_1$–$C_6$ alkoxy or phenyl.

6. A compound according to claim 5 wherein S is selected from the group consisting of trimethylsilane, triethylsilane, tripropylsilane, triisopropylsilane, dimethyl tert, butylsilane, dimethyl thexylsilane, triphenylsilane, and dimethylphenylsilane.

7. A compound according to claim 1 wherein S is a —$SiR^{10}{}_m(OSiR^{10}{}_3)_n$ wherein m=0, 1 or 2; n=3, 2 or 1; and m+n=3; or groups of the general formula IIa or IIb

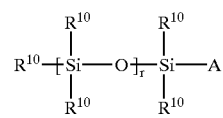

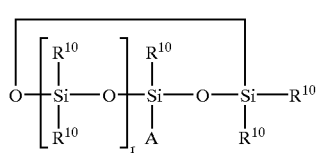

wherein
A is a bond to the linker Y;
$R^{10}$ is $C_1$–$C_6$ alkyl or phenyl;
r is 1 to 9.

8. A compound according to claim 1 wherein S is a polysiloxane group of formula IIIa or IIIb,

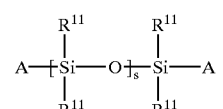

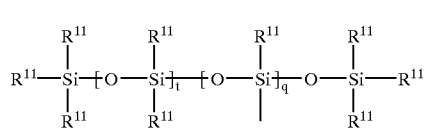

wherein
A is a bond to the linker Y;
$R^{11}$ is a $C_1$–$C_6$ alkyl or phenyl;
s is from 4 to 250;
t is from 5 to 250; and
q is from 1 to 30.

9. A compound according to claim 1 wherein $R^1$ and $R^2$ are $C_1$–$C_6$ alkyl.

10. A compound according to claim 9 wherein $R^1$ and $R^2$ are $C_1$–$C_4$ alkyl.

11. A compound according to claim 10 wherein $R^1$ and $R^2$ are methyl or YS.

12. A compound according claim 1 wherein $R^3$ is $C_1$–$C_6$ alkyl.

13. A compound according to claim 12 wherein $R^3$ is $C_1$–$C_4$ alkyl.

14. A compound according to claim 13 wherein $R^3$ is ethyl or YS.

15. A compound according to claim 1 wherein $R^4$ and $R^5$ are $C_1$–$C_6$ alkyl.

16. A compound according to claim 15 wherein $R_4$ and $R_5$ are $C_1$–$C_4$ alkyl.

17. A compound according to claim 16 wherein $R_4$ and $R_5$ are methyl.

18. A compound according to claim 1 wherein R6 is $C_1$–$C_6$ alkyl or hydrogen.

19. A compound according to claim 18 wherein $R^6$ is $C_1$–$C_4$alkyl.

20. A compound according to claim 19 wherein $R^6$ is methyl.

21. A compound according to claim 7 wherein $R^{10}$ is $C_1$–$C_6$ alkyl.

22. A compound according to claim 21 wherein $R^{10}$ is $C_1$–$C_4$ alkyl.

23. A compound according to claim 22 wherein $R^{10}$ is methyl.

24. A compound according to claim 7 wherein r is 1–3.

25. A compound according to claim 8 wherein $R^{11}$ is $C_1$–$C_6$ alkyl.

26. A compound according to claim 25 wherein $R^{11}$ is a $C_1$–$C_4$ alkyl.

27. A compound according to claim 26 wherein $R^{11}$ is a methyl group.

28. A compound according to claim 8 wherein s is 5–150.

29. A compound according to claim 8 wherein t is 5–250.

30. A compound according to claim 29 wherein t is a statistical mean value of about 60.

31. A compound according to claim 8 wherein q is 2–10.

32. A compound according to claim 31 wherein q is a statistical mean value of about 4.

33. A compound according to claim 1 wherein n is 0 or 1.

34. A light screening composition comprising a compound of formula I:

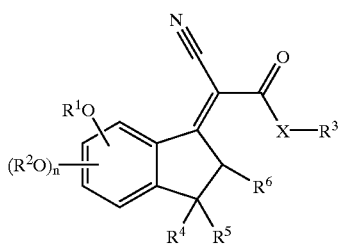

wherein

X is a O or NH;

$R^1$ is a $C_1$–$C_{20}$ alkyl, $C_2$–$C_{20}$ alkyl in which at least one methylene group is replaced by oxygen, $C_3$–$C_{20}$ alkenyl, $C_3$–$C_{20}$ alkynyl or a group YS;

$R^2$ is a $C_1$–$C_{20}$ alkyl, $C_2$–$C_{20}$ alkyl in which at least one methylene group is replaced by oxygen, $C_3$–$C_{20}$ alkenyl, $C_3$–$C_{20}$ alkynyl or a group YS; or $R^1$ and $R^2$ may combine on adjacent C-atoms to form a dioxomethylene ring;

$R^3$ is a $C_1$–$C_{20}$ alkyl, $C_2$–$C_{20}$ alkyl in which at least one methylene group is replaced by oxygen, $C_3$–$C_{20}$ alkenyl, $C_3$–$C_{20}$ alkynyl or a group YS;

$R^4$, $R^5$, $R^6$ are each independently H or $C_1$–$C_{20}$ alkyl;

n is 0, 1 or 2;

Y is a linker group;

S is a silane-, an oligosiloxane- or a polysiloxane-moiety; with the proviso that at least one of the residues $R^1$, $R^2$ or $R^3$ is YS.

35. A light screening composition according to claim 34 further comprising common UVA and/or UVB screening agents.

36. A method for protecting skin from UV damage comprising applying to the skin a light screening composition containing a compound of formula I:

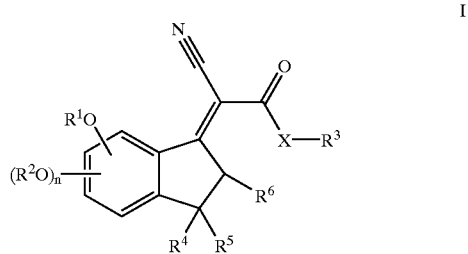

wherein

X is a O or NH;

$R^1$ is a $C_1$–$C_{20}$ alkyl, $C_2$–$C_{20}$ alkyl in which at least one methylene group is replaced by oxygen, $C_3$–$C_{20}$ alkenyl, $C_3$–$C_{20}$ alkynyl or a group YS;

$R^2$ is a $C_1$–$C_{20}$ alkyl, $C_2$–$C_{20}$ alkyl in which at least one methylene group is replaced by oxygen, $C_3$–$C_{20}$ alkenyl, $C_3$–$C_{20}$ alkynyl or a group YS; or $R^1$ and $R^2$ may combine on adjacent C-atoms to form a dioxomethylene ring;

$R^3$ is a $C_1$–$C_{20}$ alkyl, $C_2$–$C_{20}$ alkyl in which at least one methylene group is replaced by oxygen, $C_3$–$C_{20}$ alkenyl, $C_3$–$C_{20}$ alkynyl or a group YS;

$R^4$, $R^5$, $R^6$ are each independently H or $C_1$–$C_{20}$ alkyl;

n is 0, 1 or 2;

Y is a linker group;

S is a silane-, an oligosiloxane- or a polysiloxane-moiety; with the proviso that at least one of the residues $R^1$, $R^2$ or $R^3$ is YS.

* * * * *

UNITED STATES PATENT AND TRADEMARK OFFICE
CERTIFICATE OF CORRECTION

PATENT NO. : 6,416,746 B1
DATED : July 9, 2002
INVENTOR(S) : Alain Bringhen et al.

It is certified that error appears in the above-identified patent and that said Letters Patent is hereby corrected as shown below:

<u>Title page,</u>
Item [56], References Cited, OTHER PUBLICATIONS, please change
"[indan-1,3+e,acu+ee –pyrrolidine]" to -- [indan-1,3´-pyrrolidine] --.

Signed and Sealed this

Nineteenth Day of November, 2002

*Attest:*

*Attesting Officer*

JAMES E. ROGAN
*Director of the United States Patent and Trademark Office*